United States Patent [19]
Ohtsuka et al.

[11] Patent Number: 5,436,679
[45] Date of Patent: Jul. 25, 1995

[54] APPARATUS FOR OBSERVING AND PHOTOGRAPHING A CORNEAL ENDOTHELIUM

[75] Inventors: Hiroyuki Ohtsuka; Kenjirou Katsuragi; Masaru Sato; Kouji Nishio; Hiroshi Iijima, all of Tokyo, Japan

[73] Assignee: Kabushiki Kaisha TOPCON, Tokyo, Japan

[21] Appl. No.: 982,540

[22] Filed: Nov. 27, 1992

[30] Foreign Application Priority Data

Nov. 29, 1991 [JP] Japan .................. 3-316560
Dec. 9, 1991 [JP] Japan .................. 3-324247

[51] Int. Cl.[6] .............. A61B 3/14; A61B 3/10
[52] U.S. Cl. .................... 351/206; 351/221; 354/62
[58] Field of Search .............. 606/4; 128/745; 354/62; 364/413.13; 351/205, 206, 208, 211, 214, 216, 220, 221

[56] References Cited

U.S. PATENT DOCUMENTS

| | | | |
|---|---|---|---|
| 4,219,257 | 8/1980 | Slappey et al. | 351/205 |
| 4,257,687 | 3/1981 | Kohayakawa | 354/62 |
| 4,323,299 | 4/1982 | Roberts | 351/214 |
| 4,340,281 | 7/1982 | McIntyre | 351/205 |
| 4,597,650 | 7/1986 | Yoshino et al. | 351/214 |
| 4,976,535 | 12/1990 | Reis | 351/214 |

Primary Examiner—William L. Sikes
Assistant Examiner—David R. Parsons
Attorney, Agent, or Firm—Finnegan, Henderson, Farabow, Garrett & Dunner

[57] ABSTRACT

An apparatus for observing and photographing a corneal endothelium includes an illumination optical system 28 for projecting each illumination light emitted by a light source 30 for observation and a light source 32 for photography onto a cornea C of a subject's eye E at an angle, an observing and photographing optical system 29 for receiving scattered light reflected by the cornea C with the endothelial layer and observing and photographing it, and an optical system 1 for observing the anterior segment of the eye E. The observing and photographing optical system 29 is provided with a sensor 47 for detecting an image of the endothelium in focus.

19 Claims, 11 Drawing Sheets

SECTIONING DIRECTION OF THE CORNEA

APPARATUS FOR OBSERVING AND PHOTOGRAPHING A CORNEAL ENDOTHELIUM

BACKGROUND OF THE INVENTION

1. Field of the Invention

The invention relates to an apparatus for observing and photographing the endothelial layer of the cornea of a subject's eye by projecting illumination light onto the cornea.

2. Description of the Prior Art

Heretofore, there is known a contact type of apparatus for observing and photographing a corneal endothelium. In this type of apparatus, a liquid anesthetic is dropped in the subject's eye before observing and photographing it therewith. The contact type of apparatus includes a cone lens which is in contact with the surface of the cornea. The apparatus, however, has drawbacks in which the cone lens injures the cornea because of the contact of the lens with its surface and much time is consumed for photography because of disinfection of the lens or the like. To remove those drawbacks, a non-contact type of apparatus has been developed in which a slit lamp is provided with an optical attachment for observing the endothelial layer.

The non-contact type of apparatus can generally decide its position relative to the subject's eye in eye estimation. In the non-contact type of apparatus, illumination light emitted by a light source for observation is projected onto the cornea at an angle, reflected light from the cornea is guided to an eyepiece, and an operator observes the endothelial layer through the eyepiece and brings it into focus. A monitor screen can be also employed to take the focus.

By the way, the cornea itself is thin and its endothelium is composed of a single layer of thin flattened cells that lines the innermost of the cornea. Therefore, the endothelial layer thereof must be highly magnified for observation. However, such a high magnification results in a big vibration of its image caused by the continuous slight tremor of the eye. Therefore, the operator requires great skill to observe and photograph the corneal endothelial layer with the conventional non-contact type of apparatus. For example, the operator must timely push a photographing button as soon as the image is brought into focus. Further, since the non-contact type of apparatus is not predetermined to be precisely positioned relative to the eye, the operator must observe the dark field visible through the eyepiece until the image of the corneal endothelium appears or reflected light from the corneal surface is found out beside the image. This conventional apparatus largely depends on operator's experience and strong intuitive feeling.

Further, since the alignment of the optical system of the apparatus with the eye often requires much time, the subject is compelled for a long time to keep the eye open until finishing photographing it, and hence undergoes much pain.

SUMMARY OF THE INVENTION

A first object of the invention is to provide an apparatus for observing and photographing a corneal endothelium, capable of deciding the position of the optical system of the apparatus in relation to a subject's eye while observing the anterior segment of the eye.

A second object of the invention is to provide an apparatus for observing and photographing a corneal endothelium, whereby difficulties imposed on an operator and a subject are lessened to the utmost.

To accomplish the objects, a corneal endothelium observing and photographing apparatus according to claim 1 of the invention is characterized by an optical system for projecting illumination light onto the cornea of a subject's eye at an angle, an optical system for receiving reflected light from the cornea and observing and photographing it, and an optical system for observing the anterior segment of the eye. Preferably, the illumination optical system and the observing and photographing optical system are approximately symmetrical with respect to the optical axis of the eyeball of the eye. Alternatively, the two optical systems are approximately symmetrical with respect to the optical axis of the optical system for observing the anterior segment of the eye. Further, the optical system for observing the anterior segment of the eye includes an image receiving element capable of receiving both an image of the anterior segment of the eye and an image reflected from the cornea.

To accomplish the objects, a corneal endothelium observing and photographing apparatus according to claim 7 of the invention is characterized by an illumination optical system for projecting each illumination light emitted by a light source for observation and a light source for photography onto the cornea of a subject's eye at an angle, and an observing and photographing optical system for receiving reflected light from the cornea and observing and photographing it, the observing and photographing optical system being provided with a sensor for detecting an image of the corneal endothelium in focus.

Preferably, the light source for photography is connected with a light controlling circuit which is driven in response to the output of the sensor, illumination light being automatically emitted by the light source for photography in response to the output of the sensor.

To accomplish the objects, a corneal endothelium observing and photographing apparatus according to claim 9 of the invention is characterized by an illumination optical system for projecting each illumination light emitted by a light source for observation and a light source for photography onto the cornea of a subject's eye at an angle, and an observing and photographing optical system for receiving reflected light from the cornea and observing and photographing it, means for projecting index light to align the apparatus with the cornea, means for receiving the index light reflected from the cornea, and means for driving the apparatus so as to align the optical axis of the apparatus with the cornea on the basis of the output of the index light receiving means.

According to the corneal endothelium observing and photographing apparatus according to claim 1 of the invention, the corneal endothelium to be photographed can be decided during the observation of the cornea and hence time for photography can be shortened.

According to the corneal endothelium observing and photographing apparatus according to claim 7 of the invention, the sensor can judge an image of the corneal endothelium in focus or out of focus. Using the sensor, light is emitted by the light source for photography and an image thereof is automatically photographed.

According to the corneal endothelium observing and photographing apparatus according to claim 9 of the invention, the means for projecting index light for alignment projects index light for alignment onto the cornea.

The index light is reflected on the surface of the cornea, the reflected light is received by the light receiving means, and the means for driving the apparatus automatically drives the apparatus in response to the output of the index light receiving means so as to align the optical axis of the apparatus with the eye.

DESCRIPTION OF THE PREFERRED EMBODIMENT

Figure 1:
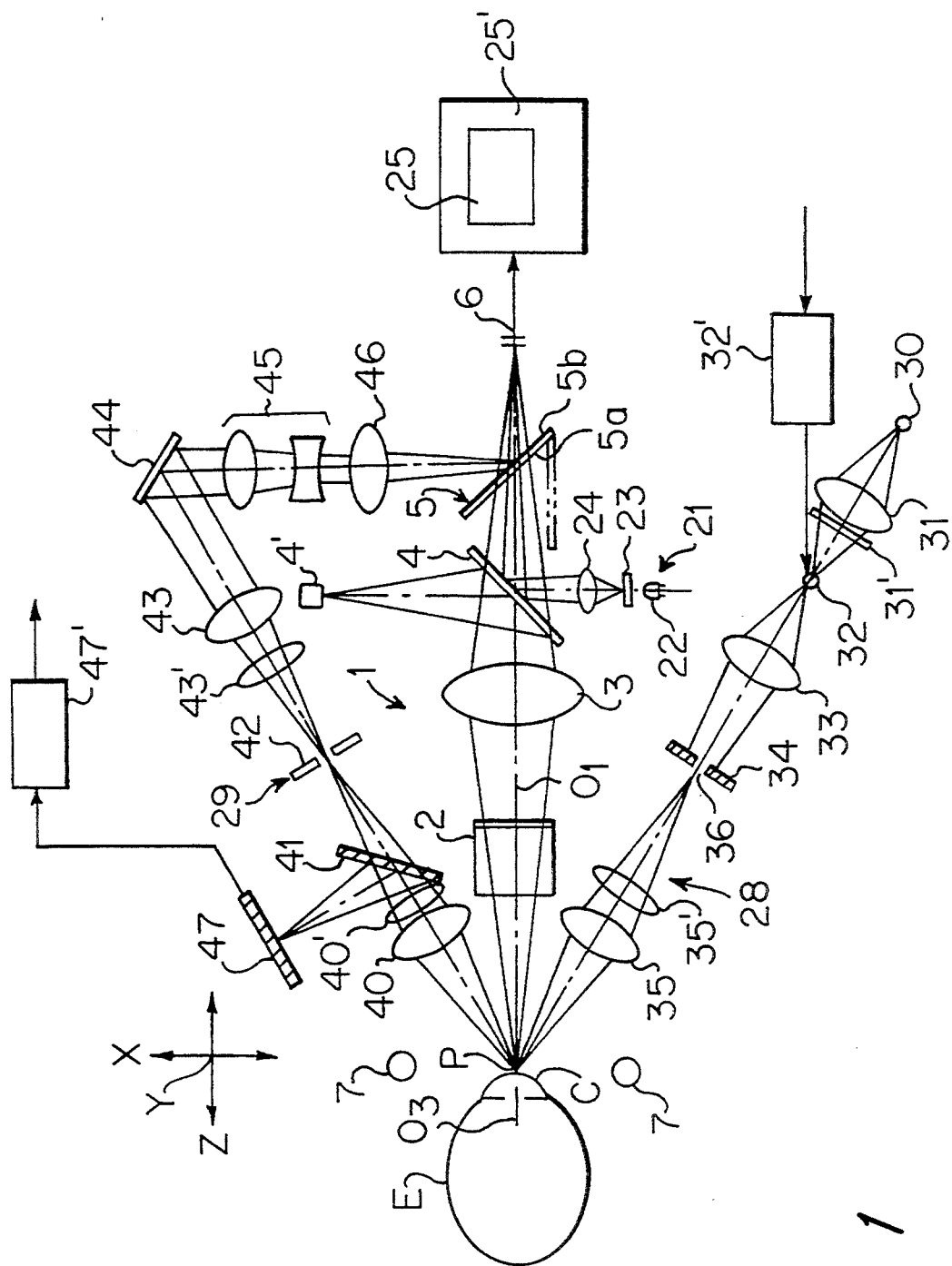
FIG. 1 shows an optical system of an embodiment of a corneal endothelium observing and photographing apparatus according to the invention.
Figure 2:
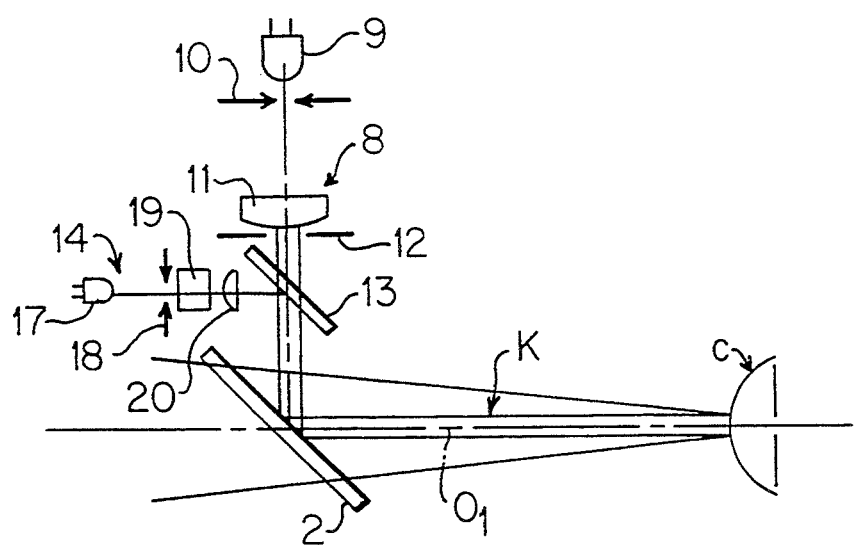
FIG. 2 shows an optical system for alignment according to the invention.

FIG. 1 is a schematic plan view showing an optical system of an apparatus for observing and photographing the endothelial layer of the cornea of a subject's eye E. The numeral 1 denotes an optical system for observing the anterior segment of the eye E. The optical system 1 includes a half mirror 2, an objective lens 3, a half mirror 4, a mirror 5 for switching an optical path, and a CCD 6. The reference $0_1$ denotes the optical axis of the optical system 1. The anterior segment of the eye E is illuminated by a light source 7. The half mirror 2 is part of an optical system 8 serving as means for projecting indices for alignment. As shown in FIG. 2, the optical system 8 includes a light source 9 for alignment, a pinhole plate 10, a projection lens 11, a diaphragm 12, and a half mirror 13. The pinhole plate 10 is disposed at the focus of the projection lens 11. After passing through the pinhole plate 10, index light is transformed into parallel rays of light by means of the projection lens 11. The parallel rays of light travel to the half mirror 2 via the half mirror 13. The parallel rays of light reflected by the half mirror 2 are guided to the cornea C of the eye E. The half mirror 13 is part of an optical system 14 serving as means for projecting indices on which the eye E is fixed.

Figure 3A:
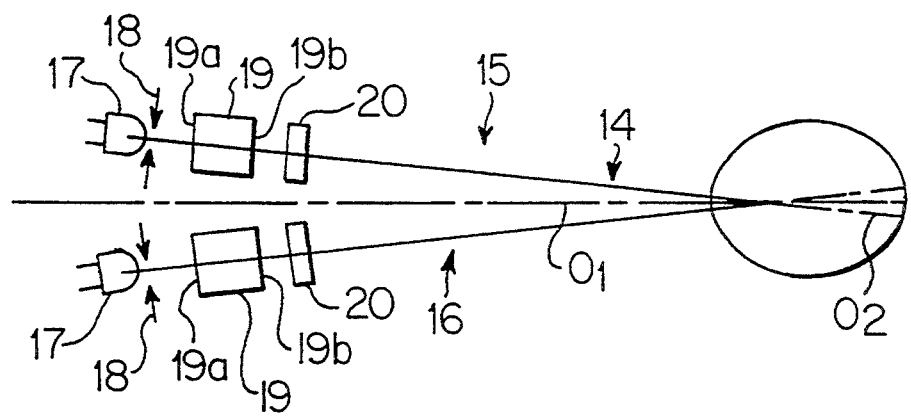
FIGS. 3(a)–(c) show an optical system for projecting an index on which a subject's eye is fixed according to the invention.
Figure 3B:
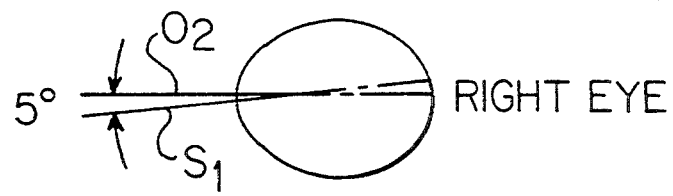
Figure 3C:
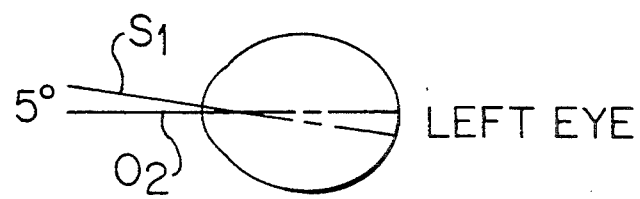

As shown in FIG. 3(a), the optical system 14 includes a projection optical system 15 for the left eye of the subject and a projection optical system 16 for the right eye thereof. The projection optical systems 15 and 16 are separately arranged in the optical system 14 for the following reason. As for the right eye, the optical axis $0_2$ of the eye forms an angle of 5° rightward with respect to the visual line $S_1$ thereof (see FIG. 3(b)) and as for the left eye, the optical axis $0_2$ of the eye forms an angle of 5° leftward with respect to the visual line $S_1$ thereof (see FIG. 3(c)). The projection optical systems 15 and 16 each include a light source 17, a pinhole plate 18, an optical member 19 for presenting a plural number of indices for fixation, and a projection lens 20. The light source 17 for the right eye is automatically turned on when the right eye is examined, whereas the light source 17 for the left eye is automatically turned on when the left eye is examined. The on-off control of the light sources 17, 17 is performed by detecting the movement of an apparatus H, which will be hereinafter described, in the right or left direction, for example. Light emitted by the light source 17 is several times reflected on surface 19a and 19b of the optical member 19. The reflected light is then projected onto the eye E through the half mirrors 13 and 2. Thereby, a plural number of indices for fixation are presented to the eye E. While the subject's eye is fixed on any index relative to the diopter, the alignment of the eye with the optical system of the apparatus H is performed.

Figure 4:
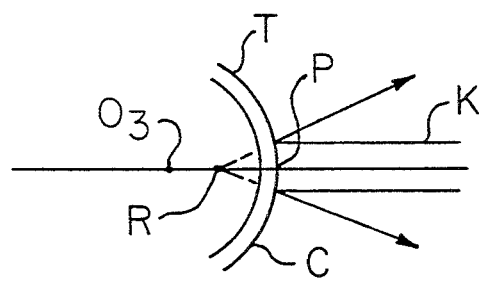
FIG. 4 shows reflection of index light for alignment according to the invention.

As shown in FIG. 4, rays of light K for alignment are reflected on the surface T of the cornea C as if they were emitted from the middle between the apex P of the cornea C and the center $0_3$ of curvature thereof. Therefore, the rays of light K for alignment forms a spot image R' at the middle between P and $0_3$. The rays of light K reflected on the surface C are guided to the objective lens 3 through the half mirror 2. Part of the rays of light K is reflected by the half mirror 4 and the remainder passes through the same 4. The rays of light reflected by the half mirror 4 are guided to a light receiving element 4' for alignment. A PSD (position sensitive device), for example, is used as a light receiving element. The function of the light receiving element 4' will be hereinafter described in detail.

Figure 5:
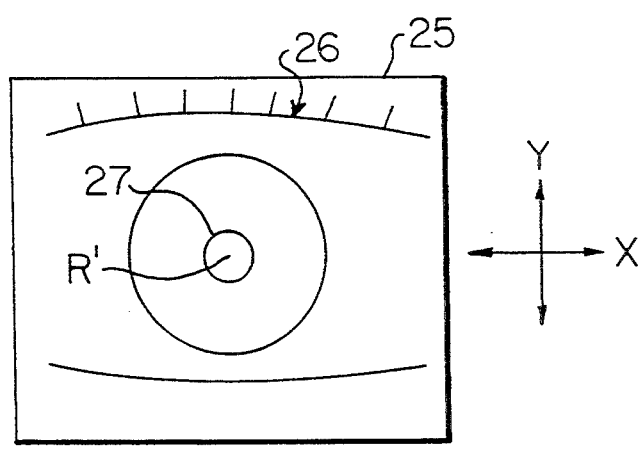
FIG. 5 shows an image of the anterior segment of the eye.
Figure 17:
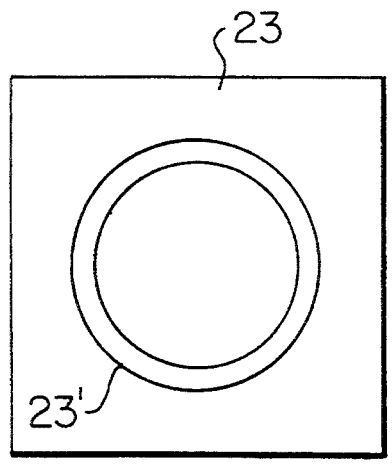
FIG. 17 is a plan view of a pattern plate of FIG. 1.

The mirror 5 for switching an optical path is usually disposed out of the optical path of the optical system 1 as shown by a phantom line in FIG. 1. The mirror 5 includes a light shading surface 5a on one side and a total reflection surface 5b on the other side. After passing through the half mirror 4, the rays of light are guided to the CCD 6 to form an image. The spot image R' is formed on the CCD 6 according to the rays of light guided thereto. At the same time, an image of the anterior segment of the eye is formed on the CCD 6. The half mirror 4 reflects rays of light emitted from an optical system 21 for projecting an alignment pattern. The optical system 21 includes a light source 22, a pattern plate 23 for alignment, and a projection lens 24. As shown in FIG. 17, an annular pattern 23' is formed in the pattern plate 23. After passing through the annular pattern 23', the rays of light are reflected by the half mirror 4 and guided to the CCD 6. Thereby, an annular pattern image is formed on the CCD 6 which is connected with a monitor 25'. The image 26 of the anterior segment of the eye E and the annular pattern image 27 are displayed on a display 25 of the monitor 25' as shown in FIG. 5.

In a manual mode, an operator carries out alignment while looking at the display 25.

First, the apparatus H is moved in the up or down direction (in the Y direction) or in the right or left direction (in the X direction) so that the spot image R' is located at the center of the annular pattern image 27. Thereby, the operator aligns the optical axis $0_2$ of the eye E with the optical axis $0_1$ of the apparatus H. The operator then moves the apparatus H toward or away from the eye E (in the Z direction) to determine an operating distance (that is, an axial distance between the apex of the cornea and the objective lens).

An optical system 28 for illumination and an optical system 29 for observation and photography are disposed on both sides of the optical system 1. The optical system 28 for illumination projects illumination light onto the cornea C of the eye E at an angle. The optical system 28 includes a light source 30 for illuminating the eye E for observation, a condenser lens 31, an infrared filter 31', a light source 32 for illuminating the eye E for photography, a condenser lens 33, a slit plate 34, a projection lens 35, and an optical member 35' for compensating an optical path. The light source 30 is conjugate with the light source 32 with respect to the condenser lens 31.

The optical member 35' is disposed in the optical system 28 for the following reason.

Owing to different wavelengths, the focal point of illumination light for observing a corneal endothelium by means of infrared rays is different from that of illumination light for photographing it by means of visible rays. Therefore, in this embodiment, a convex lens as optical member 35' is inserted into the optical path of the optical system 28 for observation by means of infrared rays, whereas the convex lens is extracted from the optical path thereof for photography by means of visible rays, in order to coincide the two focal points with each other. However, a parallel plate or concave lens as optical member 35' may be inserted into the optical path of the optical system 28 for photography by means of visible rays and be extracted therefrom for observation by means of infrared rays.

Figure 6:
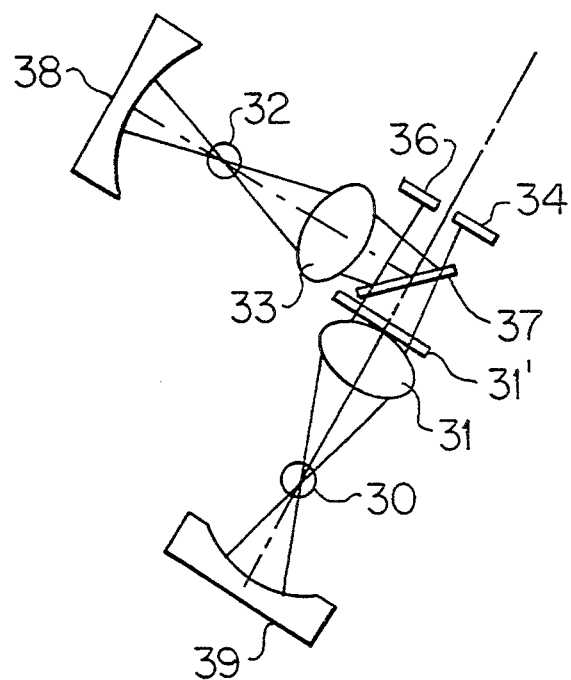
FIG. 6 shows a variant of a light source of an illumination optical system according to the invention.
Figure 18:
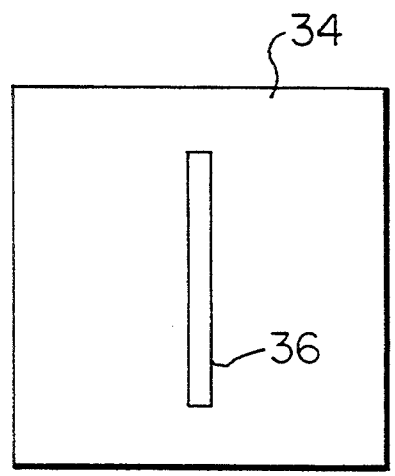
FIG. 18 is a plan view of a slit plate of FIG. 1.

For example, the light sources 30 and 32 are a halogen lamp and a xenon lamp, respectively. Rays of light emitted by the light source 30 are guided to the infrared filter 31' and transformed into infrared rays. The infrared rays are once condensed to the light source 32 and guided to the condenser lens 33 as if it were emitted by the light source 32. After passing through the condenser lens 33, the infrared rays are guided to the slit plate 34 which includes a long narrow rectangular slit 36 as shown in FIG. 18. After passing through the slit 36, they are guided to the projection lens 35. The slit plate 34 is approximately conjugate with the cornea C with respect to the projection lens 35 when aligned. Therefore, the slit infrared rays are projected onto the cornea C and they travel from the surface T of the cornea C to the inside thereof. A light source division including the light source 30, the condenser lens 31, the infrared filter 31', the light source 32, and the condenser lens 33 may be arranged as shown in FIG. 6. Referring to FIG. 6, the numerals 37, 38, and 39 denote a dichroic mirror, a concave reflecting mirror, and a concave reflecting mirror, respectively. The dichroic mirror 37 for transmitting infrared rays and reflecting visible rays is disposed between the condenser lens 31 and the slit plate 34.

Figure 7:
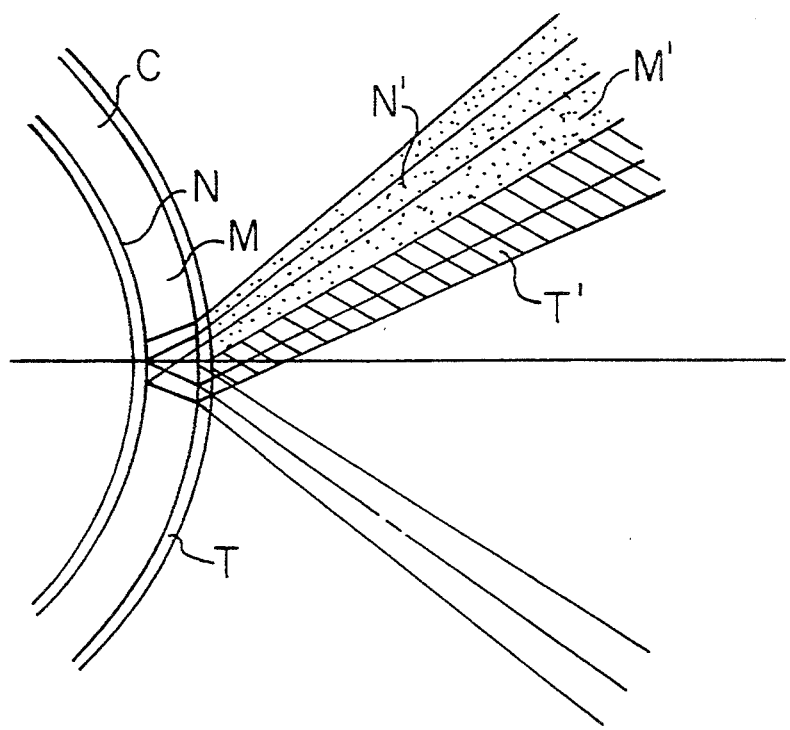
FIG. 7 shows reflection of slit light on the cornea.
Figure 19A:
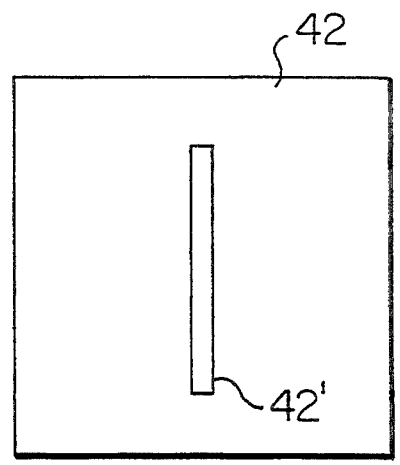
FIGS. 19(a) and (b) are each a plan view of a diaphragm of FIG. 1.
Figure 19B:
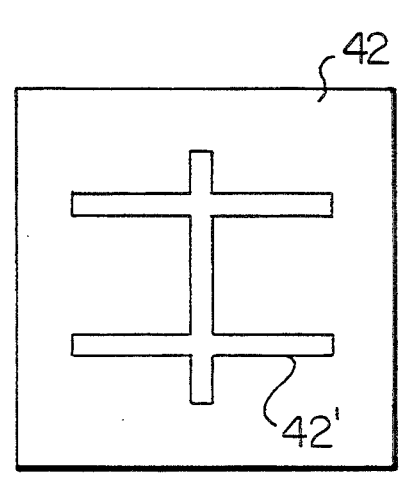

The optical system 29 for observation and photography includes an objective lens 40, a half mirror 41, a mask 42, a relay lens 43, a mirror 44, a variable power lens 45, a focusing lens 46, and a mirror 5. As shown in FIGS. 19(a) or 19(b), the mask 42 includes a slit opening 42'. The mirror 5 is automatically inserted into the optical path of the optical system 1 according to the output of the sensor 4'. The mask 42 is approximately conjugate with the cornea C with respect to the objective lens 40 when aligned. The slit light rays are reflected by the cornea C. The reflection is schematically illustrated in FIG. 7. Part of the slit light rays are first reflected on the corneal surface T as a boundary between air and the cornea C. Of all the reflected light rays from the cornea C, reflected light rays T' from the surface T have the largest quantity of light. Reflected light rays N' from the endothelial layer N have a relatively small quantity of light. Reflected light rays M' from the stromal layer M have the smallest quantity of light. The reflected light rays N' are condensed by the objective lens 40 and guided to the half mirror 41. Part of the reflected light rays from the cornea C is reflected by the half mirror 41 and guided to a line sensor 47 for detecting an image of the endothelium layer in focus. The other part passing through the half mirror 41 is guided to the mask 42. An aerial image of the endothelium N is formed at the position of the mask 42 which serves to shade light rays other than reflected light rays required to form the image of the endothelium N.

The optical system 29 includes an optical member 40' for compensating an optical path length. The optical member 40' is disposed in the optical system 29 for a similar reason to the optical member 35' in the optical system 28. In this embodiment, the optical member 40'60 is a convex lens, which is inserted into the optical path of the optical system 29 for observation by means of infrared rays and is extracted therefrom for photography by means of visible rays. However, a parallel plate or concave lens as optical member 40' may be inserted into the optical path of the optical system 29 for photography by means of visible rays and be extracted therefrom for observation by means of infrared rays.

Figure 8:
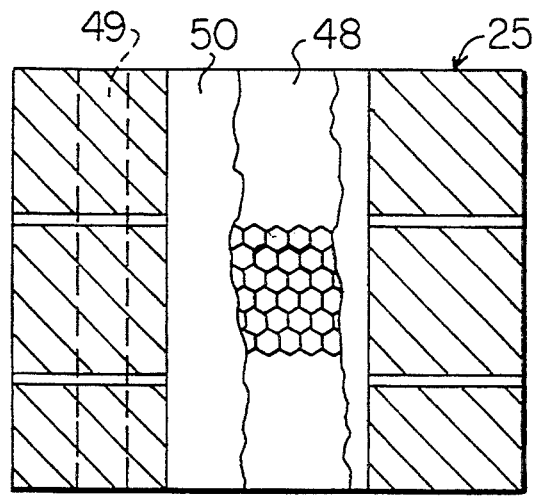
FIG. 8 shows an image of the corneal endothelium.

The reflected light rays for forming the image of the endothelial layer N are guided to the mirror 5 through the relay lens 43, the mirror 44, the variable power lens 45, and focusing lens 46. They are then reflected by the mirror 5 and focused on the CCD 6. Thereby, the image of the endothelial layer N is displayed on the display 25 as shown in FIG. 8. Referring to FIG. 8, the numeral 49 indicated in a stitch line denotes a bright image formed by the light rays reflected by the corneal surface T and the numeral 50 denotes an image formed by the light rays reflected by the stromal layer M, on the assumption that the mask 42 transmits all the reflected light rays.

Figure 9A:
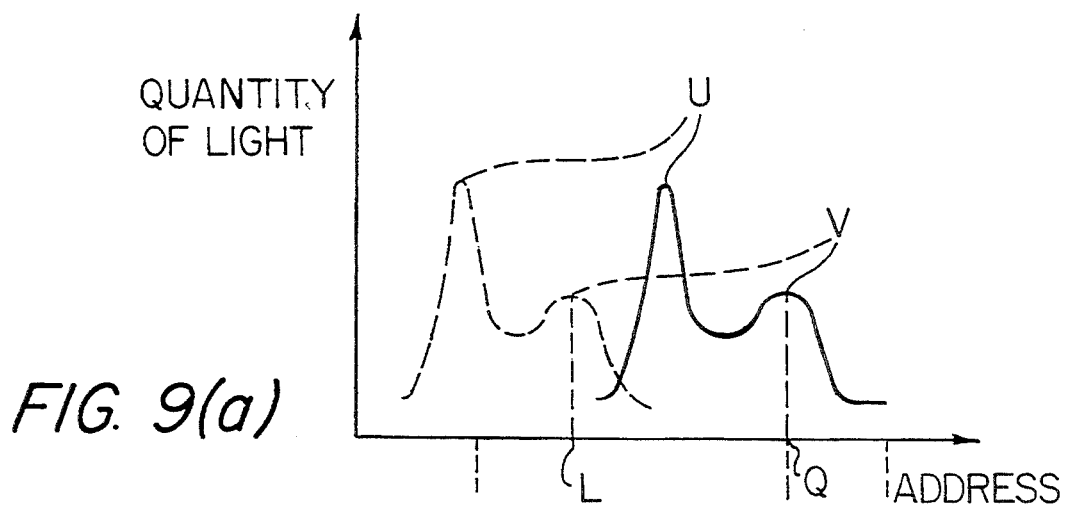
FIGS 9(a) and 9(b) the relation between the image of the corneal endothelium and the quantity of light received by a line sensor.
Figure 9B:
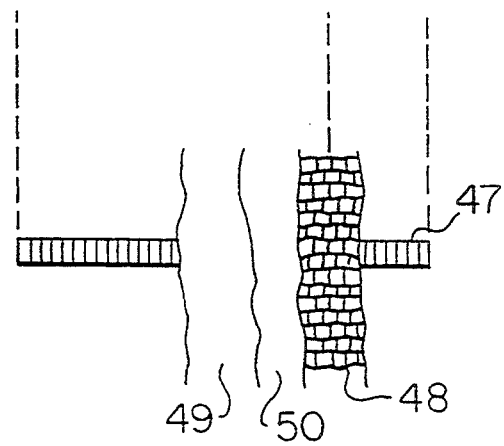
Figure 10:
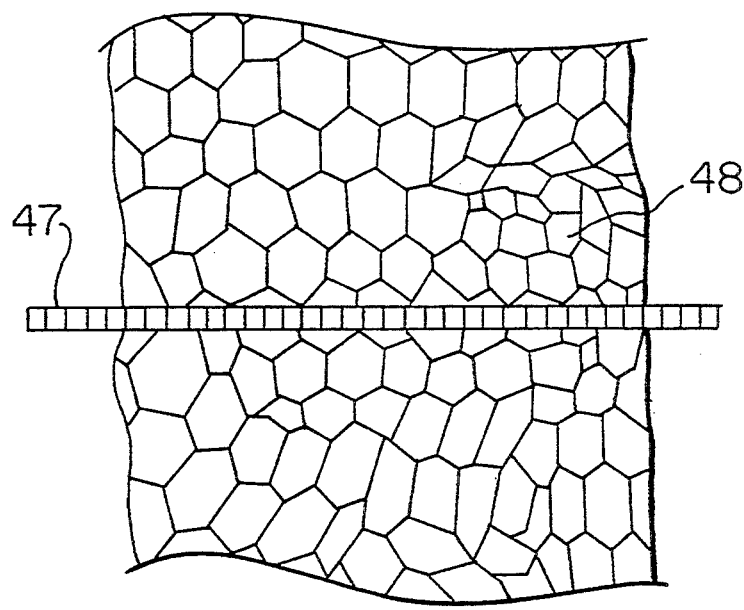
FIG. 10 illustrates another method of detecting the image of the corneal endothelium in or out of focus.

Toward the respective layers of the cornea, the line sensor 47 is arranged as shown in FIG. 9(b). Therefore, with respect to the line sensor 47, the intensity of the reflected light rays is distributed as shown in FIG. 9(a). Referring to FIG. 9(a), the reference character U denotes the peak intensity of the light rays reflected by the corneal surface I and the reference character V denotes the peak intensity of the light rays reflected by the endothelial layer N. The peaks U and V correspond to the images 49 and 48, respectively.

As shown in FIG. 1, the output of an element in each address of the line sensor 47 is input to a focusing judgment circuit 47' for judging an image of the endothelium in focus or out of focus. The focusing judgment circuit 47' memorizes signals corresponding to the intensity shown in FIG. 9(a). The focusing judgment circuit 47' decides the address of the peak V by means of an arithmetic processor as a well-known means. To judge whether the apparatus H and the eye E are properly located to gain exact focusing, the focusing judgment circuit 47' detects the coincidence of the address L of the peak V with a given address (the central address, for example) of the line sensor 47. That is, the address L of the peak V is changed by moving the apparatus H toward or away from the anterior segment of the eye E (that is, by moving the optical system of the apparatus in the Z direction in FIG. 1). The apparatus H is arranged so that the corneal endothelium N is in focus when the address L of the peak V coincides with the central address Q. Supposing that the peak v is positioned at the address L of the line sensor 47 as shown in a stitch line in FIG. 9, the address L approaches the central address Q by moving the apparatus H toward the eye E. When the address L of the peak V coincides with the central address Q, the focusing judgment circuit 47' outputs photographing signals toward a control circuit 32' for turning on the light source 32. Thereby, light rays are emitted by the light source 32, the eye is illuminated, and an image of the endothelium is automatically taken. Preferably, the light source 30 is turned off when photographed.

Figure 11:
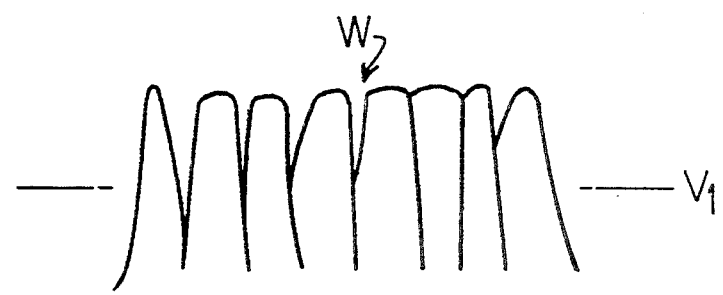
FIG. 11 shows the output of the line sensor of FIG. 10.

A judgment whether the image 48 of the endothelium N is in focus or out of focus may be formed in the following way. The image 48 is formed at the line sensor 47. When the image 48 is out of focus, the output of each element of the line sensor 47 is low. When in focus, the image 48 at the line sensor 47 is good in contrast, and hence the intensity of the reflected light rays from the cornea C is distributed with respect to the line sensor 47 as shown in FIG. 11. Therefore, a judgment as to the image 48 is focus or out of focus is formed by detecting a level W of the signal of each element of the line sensor 47 more than a given level $V_1$.

Figure 12:
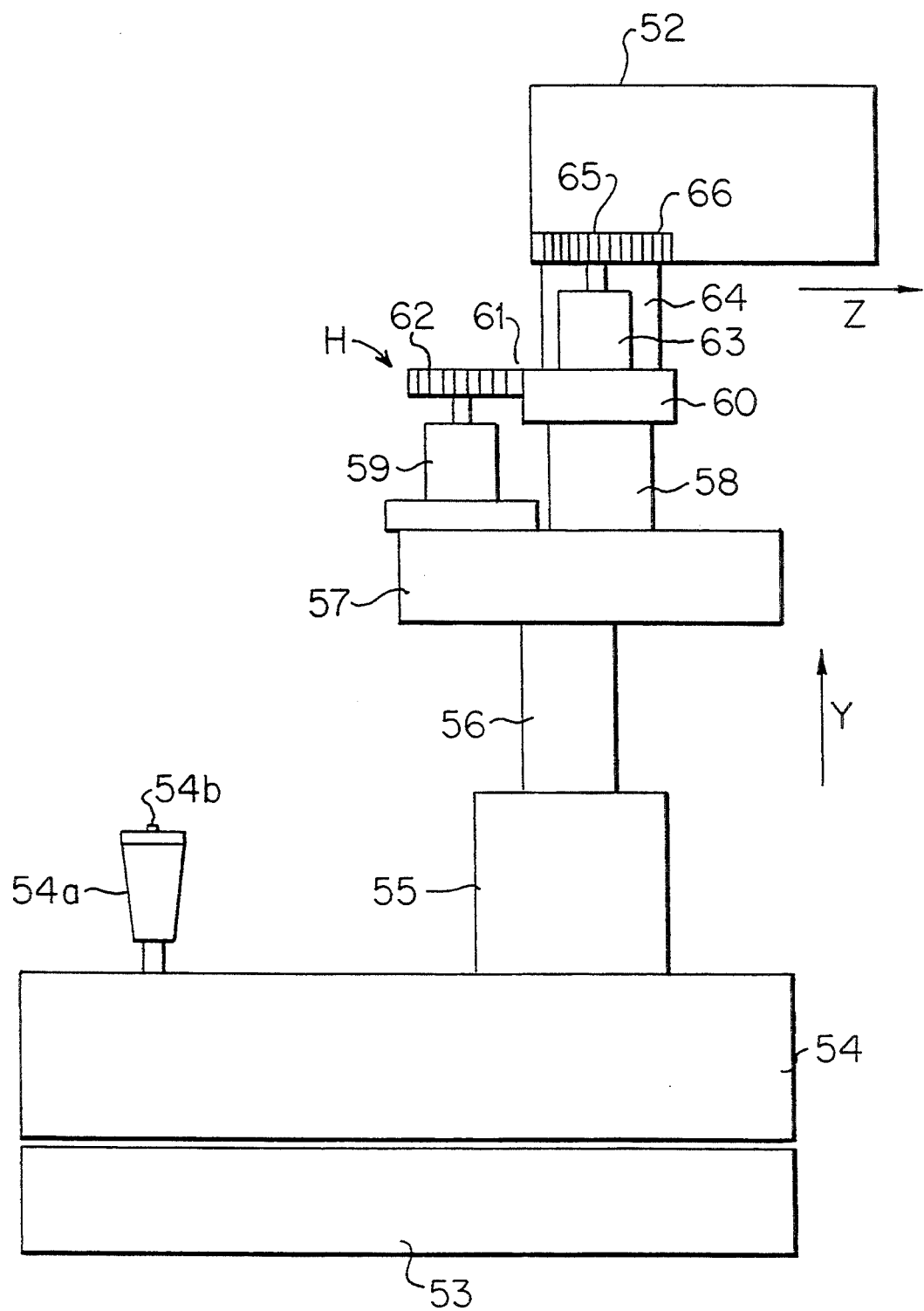
FIG. 12 is a side view showing the whole construction of the apparatus according to the invention.
Figure 13:
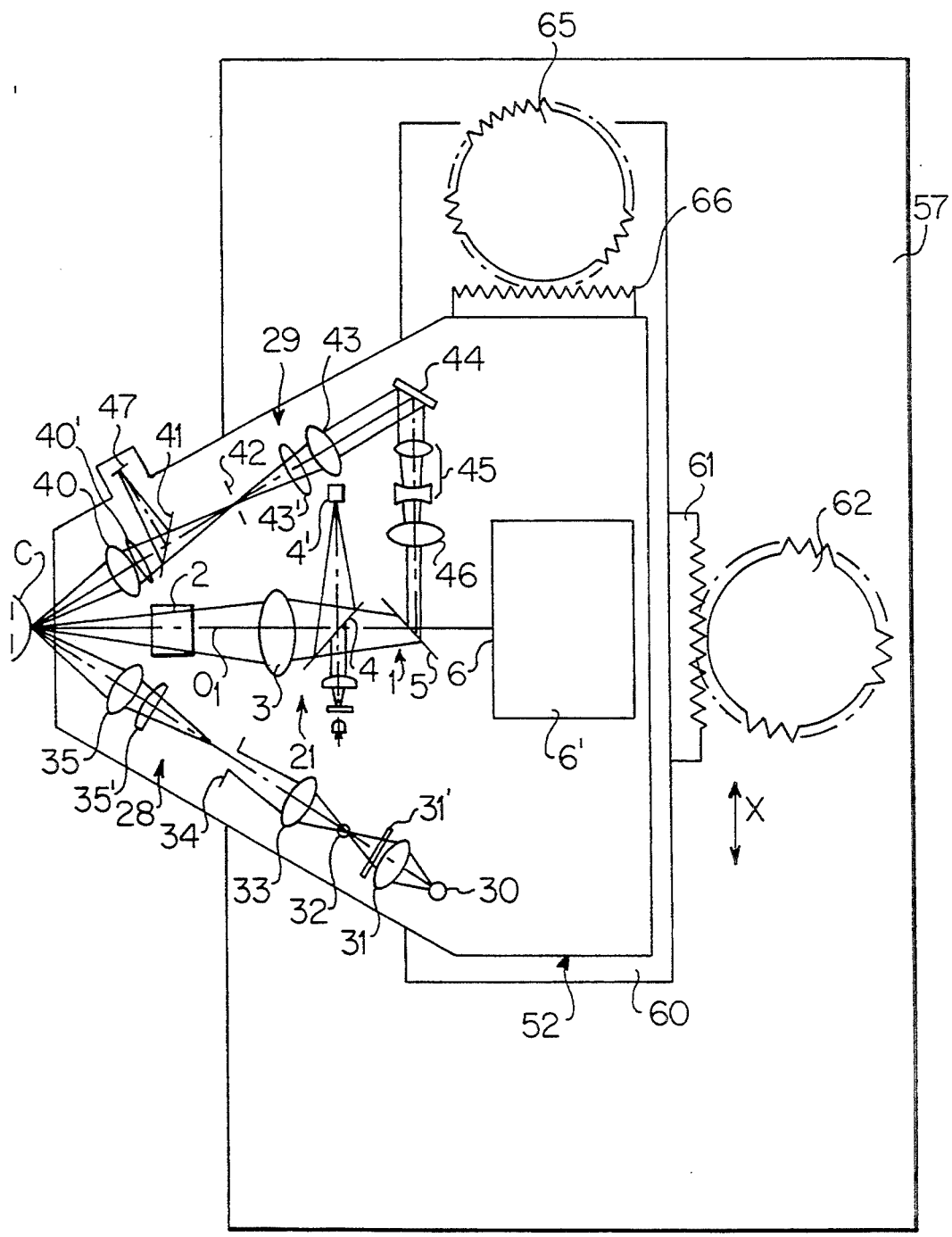
FIG. 13 is a fragmentary top view of the apparatus according to the invention.

As shown in FIG. 12, the optical systems 1, 28, and 29 are contained in a case 52 of the apparatus H. An electric source, not shown, is contained in a base 53. A frame 54 is mounted on the base 53 so as to move in all directions. The numerals 54a and 54b denote a control lever for the frame 54 and a photographing switch for a manual photographing mode, respectively. A motor 55 and a pillar 56 are mounted on the frame 54. The motor 55 is connected with the supporting pillar 56 by a pinion and a rack, not shown. The supporting pillar 56 is moved up or down by the motor 55. A pillar 58 and a motor 59 are mounted on a table 57. A table 60 is movably mounted on the pillar 58. As shown in FIG. 13, a rack 61 is disposed behind the table 60. A pinion 62 is connected with an output shaft of the motor 59. The pinion 62 is engaged with the rack 61. A motor 63 and a pillar 64 are mounted on the table 60. A pinion 65 is connected with an output shaft of the motor 63. A case 52 is movably mounted on the pillar 64. A rack 66 is disposed at the side of the case 52. The rack 66 is engaged with the pinion 65. In FIG. 13, the numeral 6' denotes a signal processing unit.

The motor 55 serves to automatically align the apparatus H in the Y direction with the eye E, the motor 59 serves to automatically align the apparatus H in the X direction therewith, and the motor 63 serves to automatically align the apparatus H in the Z direction therewith. These motors 55, 59, and 63 can work by an automatic photographing mode. In other words, the motors 55, 59, and 63 each serve as a means for driving the apparatus H according to the output of a light receiving means.

Figure 14:
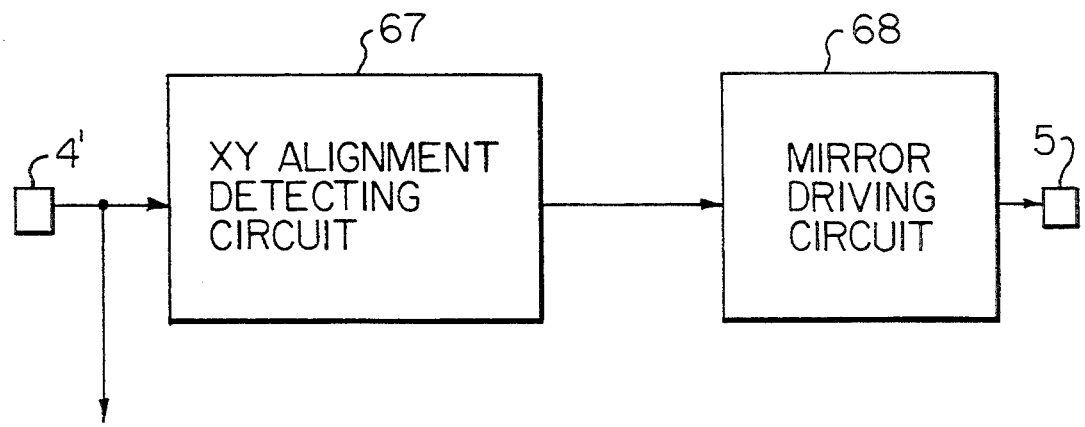
FIG. 14 shows a driving circuit for driving a mirror for switching an optical path.

In the automatic photographing mode, the operator handles the control lever 54a while looking at the image 26 of the anterior segment of the eye E and the spot image R' displayed on the display 25 in order to move the frame 54 and bring the spot image R' close to a given circle 27. Thereby, the reflected light rays for forming the spot image R' are guided to the sensor 4'. The sensor 4' detects positions of the spot image R' in the X and Y directions. The positions detected thereby are input into a detection circuit 67, shown in FIG. 14, for alignment in the X and Y directions. Immediately after completing each alignment in the X and Y directions, the detection circuit 67 outputs an alignment completion signal to a mirror driving circuit 68 by the signal of which the mirror 5 is inserted into the optical path of the optical system 1.

Position signals of the X and Y directions detected by the sensor 4' are input into a signal processing circuit 6'. The signal processing circuit 6' drives the motor 59 according to the position signal of the X direction so that the optical axis $0_1$ of the optical system 1 approaches the optical axis $0_2$ of the eye E in the X direction. Also, the signal processing circuit 6' drives the motor 55 according to the position signal of the Y direction so that the optical axis $0_1$ of the optical system 1 approaches the optical axis $0_2$ of the eye E in the Y direction. The table 60 is moved in the X direction by the motor 59, whereas the table 57 is moved in the Y direction by the motor 55. In such a way, the optical axes $0_1$ and $0_2$ are automatically adjusted to each other. On the other hand, the motor 63 moves the case 52 in the Z direction according to a difference between the respective addresses Q and L detected by the one-dimensional line sensor 47 so that the address L of the peak coincides with the central address Q. Thereby, the alignment of the optical system of the apparatus H with the eye E is automatically completed and then the corneal endothelium N is automatically photographed.

Figure 15:
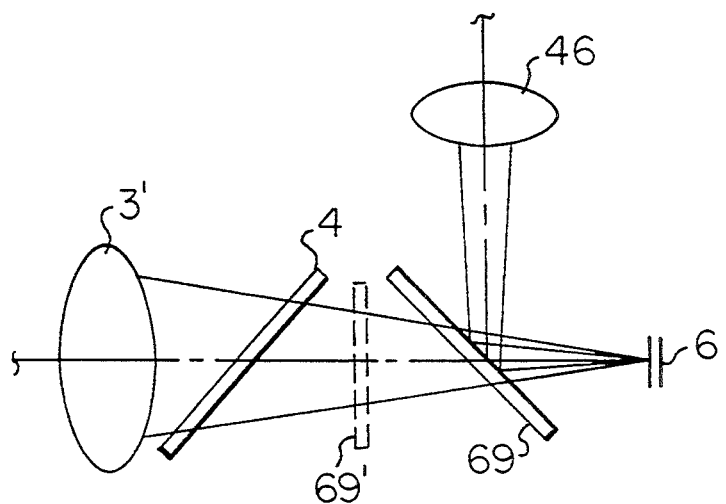
FIG. 15 shows a variant of the apparatus provided with a dichroic mirror instead of the mirror for switching an optical path of FIG. 1.

FIG. 15 shows another embodiment of a corneal endothelium observing and photographing apparatus according to the invention. In this embodiment, a dichroic mirror 69 is used instead of the mirror 5. The light source 7 for illuminating the anterior segment of the eye for observation is of infrared rays. Index light rays for alignment and light rays for forming a pattern image are also infrared rays. The dichroic mirror 69 serves to transmit index light rays for alignment reflected by the cornea C and light rays reflected by the anterior segment of the eye E and to reflect slit light rays reflected by the cornea C. Such an arrangement permits a display image to be switched from an image 26 of the anterior segment to an image 48 of the corneal endothelium without moving the dichroic mirror 69. In other words, images of the anterior segment, of the spot, and of the pattern can disappear from the display 25 by turning off the light sources 7, 9, and 22. To vanish the images therefrom without turning off the light sources, between the half mirror 4 and the dichroic mirror 69 may be disposed a liquid crystal shutter 69' for shading such light rays simultaneously with the completion of each alignment in the X and Y directions.

Figure 16:
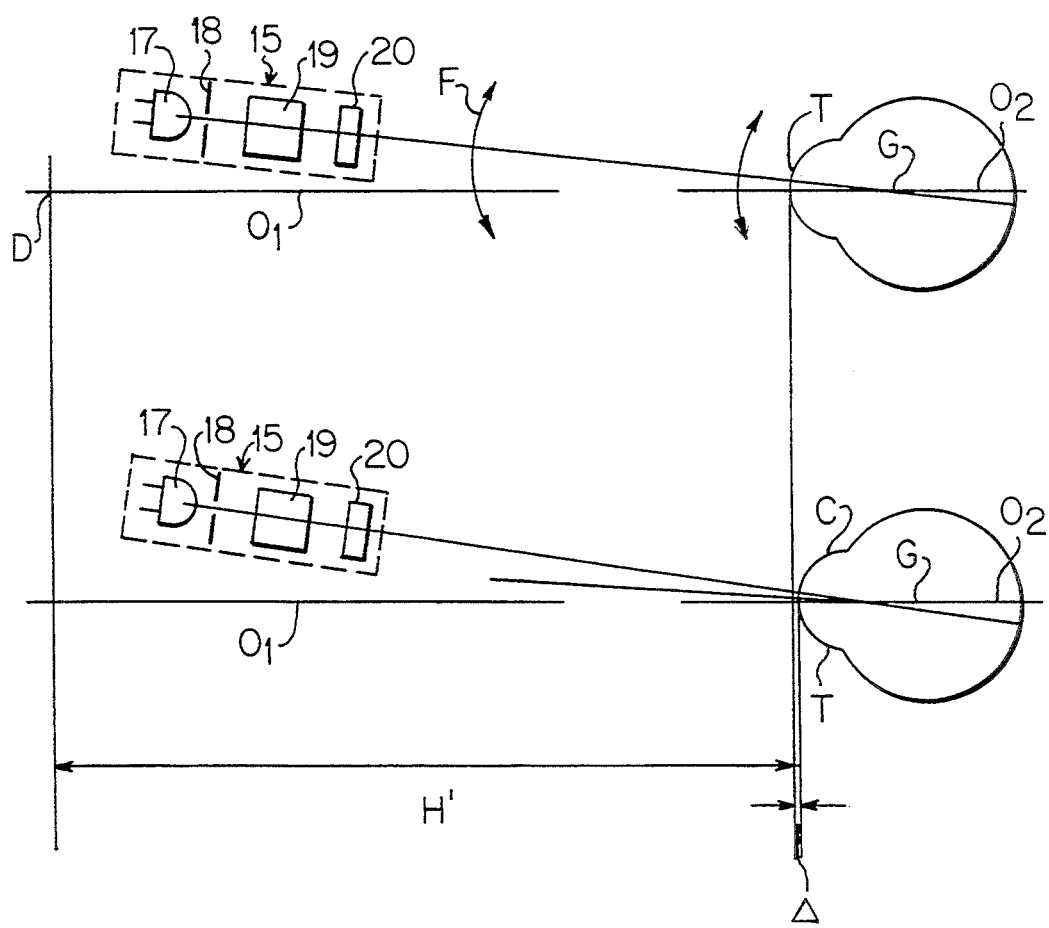
FIG. 16 illustrates a method of focusing on the corneal endothelium using the optical system for projecting an index for eye's fixation according to the invention.

FIG. 16 shows an embodiment of fine adjustment for achieving exact focusing of the image 48 of the corneal endothelium. After making manual adjustment for alignment, the optical system 14 is turned in the direction of the arrow F and the eyeball of the eye E is revolved in the same direction as the arrow F on a rotating center G. In proportion to its rotation, a distance H' from a standard point D of the objective lens 3 to the surface T of the cornea C is altered, and thus alternation varies focusing of the image 48 of the endothelium. The reference character Δ denotes a variation of the distance H'.

What is claimed is:

1. An apparatus for observing and photographing a corneal endothelium, comprising:
    anterior segment observing optical system means for frontally observing an anterior segment of a subject's eye;
    said anterior segment observing optical system means having an optical axis normal to a reference plane tangent to a surface of the cornea of the subject's eye;
    illumination light projecting optical system means for projecting illumination light onto a cornea of a subject's eye;
    photographing optical system means for photographing a corneal endothelium of the subject's eye; and
    an optical path of said anterior segment observing optical system means being separated from an optical path of said photographing optical system means.

2. An apparatus for observing and photographing a corneal endothelium comprising:
    anterior segment observing optical system means for frontally observing an anterior segment of a subject's eye;
    said anterior segment observing optical system means having an optical axis normal to a reference plane tangent to a surface of the cornea of the subject's eye;
    illumination light projecting optical system means for projecting illumination light onto a cornea of the subject's eye obliquely with respect to an optical axis of said anterior segment observing optical system means; and
    observing and photographing optical system means for receiving a reflected image, which includes an endothelium image of said cornea from said cornea, obliquely with respect to the optical axis of said anterior segment observing optical system means and observing and photographing a corneal endothelium of the subject's eye, said observing and photographing optical system means being disposed on the opposite side of the optical axis of said anterior segment observing optical system means with respect to said illumination light projecting optical system means.

3. An apparatus for observing and photographing a corneal endothelium according to claim 2, wherein an angle formed between the optical axis of said anterior segment observing optical system means and an optical axis of said illumination light projecting optical system means is substantially equal to an angle formed between the optical axis of said anterior segment observing optical system means and an optical axis of said observing and photographing optical system means.

4. An apparatus for observing and photographing a corneal endothelium according to claim 2, wherein said anterior segment observing optical system means include image receiving element means capable of receiving an image of said anterior segment, which includes a pupil of the subject's eye, and the reflected image of said cornea.

5. An apparatus for observing and photographing a corneal endothelium according to claim 4, wherein an optical member for compensating an optical path length on the basis of a difference of wavelengths of illumination light is detachably disposed at least in the optical path of said observing and photographing optical system means.

6. An apparatus for observing sand photographing a corneal endothelium according to claim 2, wherein said illumination light projecting optical system means includes a light source for observation and a light source for photography, said light source for observation emitting infrared light and said light source for photography emitting visible light.

7. An apparatus for observing and photographing a corneal endothelium, comprising:
    illumination light projecting optical system means for projecting illumination light onto a cornea of a subject's eye;
    photographing optical system means for receiving a reflected image from said cornea and photographing an endothelium of said cornea; and
    a sensor for detecting an image of said corneal endothelium in focus.

8. An apparatus for observing and photographing a corneal endothelium according to claim 7, wherein said sensor is disposed in said photographing optical system means.

9. An apparatus for observing and photographing a corneal endothelium according to claim 7, wherein said illumination light projecting optical system means includes a light source for observation and a light source for photography, said light source for observation emitting infrared light and said light source for photography emitting visible light.

10. An apparatus for observing and photographing a corneal endothelium according to claim 9, wherein said light source for photography is automatically turned on to emit visible light based on an output of said sensor.

11. An apparatus for observing and photographing a corneal endothelium comprising:
    illumination light projecting optical system means for projecting illumination light onto a cornea of a subject's eye;
    photographing optical system means for receiving a reflected image from said cornea and photographing an endothelium of said cornea;
    a sensor for detecting an image of said corneal endothelium in focus;
    means for projecting index light to align said apparatus with said cornea;
    means for receiving index light reflected by said cornea; and
    means for driving said apparatus so as to align said optical systems with said cornea on the basis of an output of said means for receiving index light.

12. An apparatus for observing and photographing a corneal endothelium according to claim 11, wherein said light source for photography is automatically turned on to emit visible light based on an output of said sensor.

13. An apparatus for observing and photographing a corneal endothelium according to claim 11, wherein a distance between the subject's eye and said apparatus is automatically adjusted based on an output of said sensor.

14. An apparatus for observing and photographing a corneal endothelium according to claim 11, further comprising means for switching an optical path for receiving an image of an anterior segment of the subject's eye and an optical path for receiving an image of said corneal endothelium with each other on the basis of an output of said means for receiving index light.

15. An apparatus for observing and photographing a corneal endothelium comprising:
   anterior segment observing optical system means for frontally observing an anterior segment of a subject's eye;
   said anterior segment observing optical system means having an optical axis normal to a reference plane tangent to a surface of the cornea of the subject's eye;
   illumination light projecting optical system means for projecting illumination light onto a cornea of the subject's eye obliquely with respect to an optical axis of said anterior segment observing optical system means;
   observing and photographing optical system means for receiving a reflected image, which includes an endothelium image of said cornea, from said cornea obliquely with respect to the optical axis of said anterior segment observing optical system means and observing and photographing a corneal endothelium of the subject's eye, said observing and photographing optical system means disposed on the opposite side of the optical axis of said anterior segment observing optical system means with respect to said illumination light projecting optical system means;
   index projecting optical system means for projecting indices, on which the subject's eye is fixed, onto the subject's eye;
   means for projecting index light to align said apparatus with said cornea; and
   means for receiving index light reflected by said cornea.

16. An apparatus for observing and photographing a corneal endothelium according to claim 15, further comprising a sensor for detecting an image of said corneal endothelium in focus.

17. An apparatus for observing and photographing a corneal endothelium according to claim 15, further comprising means for driving said apparatus so as to align said optical systems with said cornea on the basis of an output of said means for receiving index light.

18. An apparatus for observing and photographing a corneal endothelium according to claim 15, wherein said illumination light projecting optical system means includes a light source for observation and a light source for photography, said light source for observation emitting infrared light and said light source for photography emitting visible light.

19. An apparatus for observing and photographing a corneal endothelium comprising:
   anterior segment observing optical system means for frontally observing an anterior segment, which includes a pupil of a subject's eye;
   said anterior segment observing optical system means having an optical axis normal to a reference plane tangent to a surface of the cornea of the subject's eye;
   illumination light projecting optical system means for projecting illumination light onto a cornea of the subject's eye obliquely with respect to an optical axis of said anterior segment observing optical system; and
   photographing optical system means for receiving a reflected image, which includes an endothelium image of said cornea, from said cornea obliquely with respect to the optical axis of said anterior segment observing optical system means and observing and photographing a corneal endothelium of the subject's eye, said photographing optical system means disposed on the opposite side of the optical axis of said anterior segment observing optical system means with respect to said illumination light projecting optical system means.

* * * * *